(12) United States Patent
Pedicini

(10) Patent No.: US 11,864,808 B2
(45) Date of Patent: Jan. 9, 2024

(54) GAS SPRING SURGICAL IMPACTING TOOLS

(71) Applicant: DePuy Synthes Products, Inc., Raynham, MA (US)

(72) Inventor: Christopher Pedicini, Franklin, TN (US)

(73) Assignee: DePuy Synthes Products, Inc., Raynham, MA (US)

( * ) Notice: Subject to any disclaimer, the term of this patent is extended or adjusted under 35 U.S.C. 154(b) by 127 days.

(21) Appl. No.: 17/220,431

(22) Filed: Apr. 1, 2021

(65) Prior Publication Data

US 2022/0313337 A1 Oct. 6, 2022

(51) Int. Cl.
*A61B 17/92* (2006.01)
*A61B 17/00* (2006.01)

(52) U.S. Cl.
CPC .... *A61B 17/92* (2013.01); *A61B 2017/00544* (2013.01); *A61B 2017/925* (2013.01)

(58) Field of Classification Search
CPC ...................... A61B 17/92; A61B 2017/00398
See application file for complete search history.

(56) References Cited

U.S. PATENT DOCUMENTS

| | | | | |
|---|---|---|---|---|
| 4,016,873 A * | 4/1977 | Anderson | ............... | A61H 23/04 601/107 |
| 4,298,074 A * | 11/1981 | Mattchen | ........... | A61B 17/1624 606/104 |
| 4,716,890 A * | 1/1988 | Bichel | .................... | A61H 23/04 601/108 |
| 5,057,112 A * | 10/1991 | Sherman | ............ | A61B 17/1659 606/86 R |
| 5,485,887 A * | 1/1996 | Mandanis | .............. | B25D 17/06 173/91 |
| 8,393,409 B2 | 3/2013 | Pedicini | | |
| 8,695,726 B2 | 4/2014 | Pedicini | | |
| 8,936,105 B2 | 1/2015 | Pedicini | | |
| 10,028,754 B2 * | 7/2018 | Johnson | ............. | A61B 17/1659 |
| 10,052,747 B2 * | 8/2018 | Aoki | .................... | B25D 11/005 |
| 2009/0020299 A1 * | 1/2009 | Manschitz | ........... | B25D 11/125 173/217 |
| 2013/0161050 A1 | 6/2013 | Pedicini | | |
| 2017/0100829 A1 | 4/2017 | Pedicini et al. | | |
| 2018/0055518 A1 | 3/2018 | Pedicini | | |
| 2018/0055552 A1 | 3/2018 | Pedicini | | |

(Continued)

FOREIGN PATENT DOCUMENTS

WO WO-2016112397 A1 7/2016

OTHER PUBLICATIONS

International Search Report and Written Opinion for Intl. Pat. App. No. PCT/EP2022/058771 dated Jul. 27, 2022.

*Primary Examiner* — David W Bates

(57) ABSTRACT

Various exemplary gas spring surgical impacting tools and methods of using gas spring surgical impacting tools are provided. In general, a surgical impacting tool includes a gas spring assembly. The gas spring assembly includes a sealed chamber configured to contained compressed gas therein. The surgical impacting tool also includes a motor configured to cause compression of the gas in the sealed chamber. The compression and decompression of the gas is configured to drive movement of a surgical implement attached to the surgical impacting tool and configured to impact bone.

9 Claims, 6 Drawing Sheets

(56) References Cited

U.S. PATENT DOCUMENTS

| | | |
|---|---|---|
| 2018/0055554 A1 | 3/2018 | Pedicini |
| 2018/0264636 A1* | 9/2018 | Geiger ................... B25D 17/02 |
| 2018/0338751 A1 | 11/2018 | Pedicini |
| 2019/0183555 A1* | 6/2019 | Pedicini .................. A61F 2/461 |
| 2019/0282286 A1* | 9/2019 | Pedicini ............... B25D 11/125 |

* cited by examiner

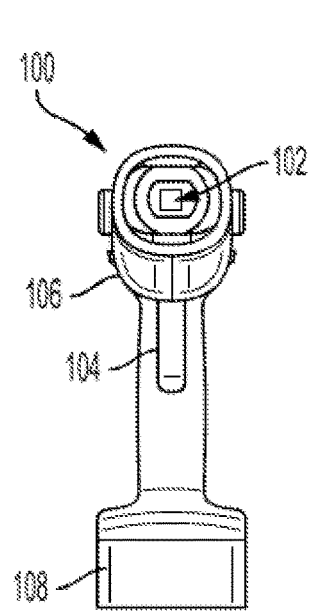
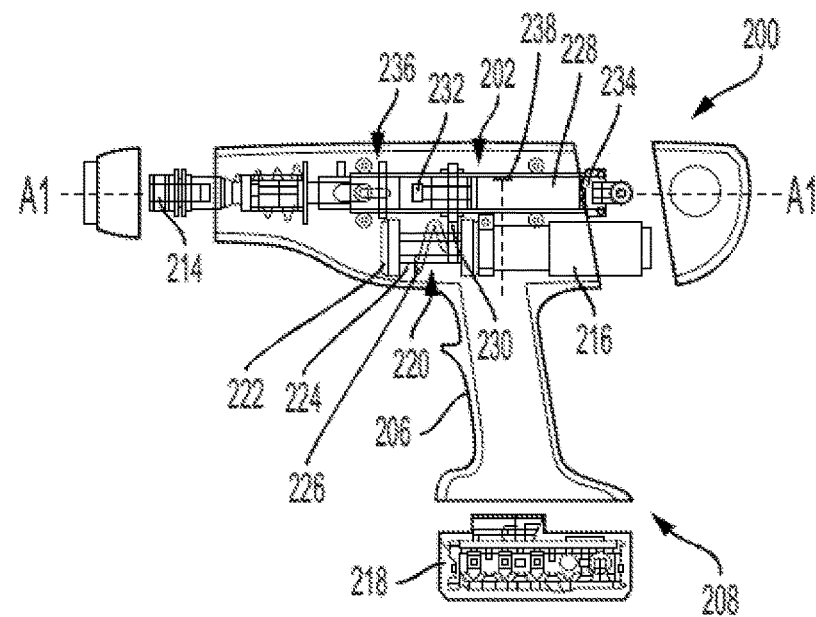
FIG. 3
FIG. 4
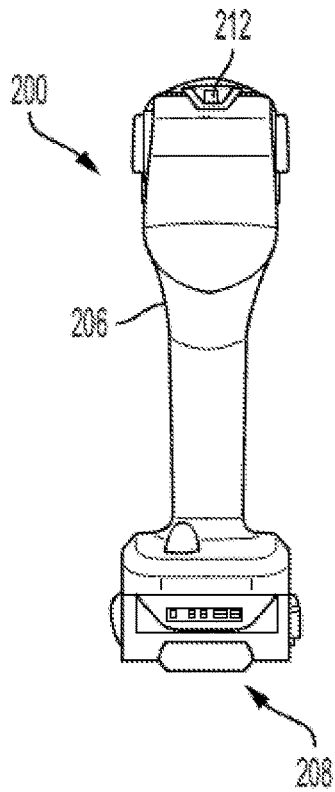
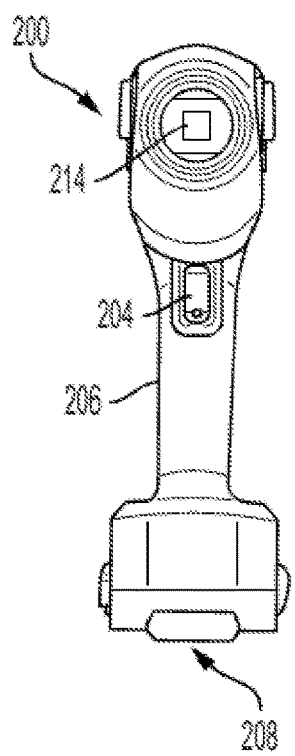
FIG. 5
FIG. 6

GAS SPRING SURGICAL IMPACTING TOOLS

FIELD

The present disclosure relates generally to gas spring surgical impacting tools.

BACKGROUND

In the field of orthopedics, prosthetic devices, such as artificial joints, are often implanted or seated in a patient's bone cavity. The cavity is typically formed during surgery before a prosthetic device is seated or implanted by, for example, a physician or other medical professional removing and/or compacting existing bone to form the cavity. The prosthetic device, which can also be referred to as a prosthesis, usually includes a stem or other protrusion that is inserted into the cavity.

To create the cavity, a physician or other medical professional may use a broach conforming to the shape of the stem of the prosthetic device. The broach can have a handle for manual hammering by the physician or other medical professional during surgery to impel the broach into the implant area. Unfortunately, this approach is crude and notoriously imprecise, leading to unnecessary mechanical stress on the bone and highly unpredictable depending upon the skill of a particular medical professional. Historically, this brute force approach will in many cases result in inaccuracies in the location and configuration of the cavity. Additionally, the medical professional is required to expend an unusual amount of physical force and energy to hammer the broach and to manipulate the bones and prosthesis. This approach also carries with it the risk that the medical professional will cause unnecessary further trauma to the surgical area and/or damage otherwise healthy tissue, bone structure, and/or the like.

Another technique for creating the prosthetic cavity is to drive a broach pneumatically, e.g., by compressed air. However, this approach limits, if not entirely prevents, portability of an impacting tool because of the presence of a tethering air-line. Additionally, this approach can result in air being exhausted from a tool into the sterile operating field, can result in fatigue of the medical professional operating the tool, and/or does not allow for precise control of the impact force or frequency and instead functions very much like a jackhammer when actuated. Again, this lack of any measure of precise control makes accurate broaching of the cavity more difficult and leads to unnecessary patient complications and trauma.

Another technique for creating the prosthetic cavity relies on a linear compressor to compress air on a single stroke basis and then, after a sufficient pressure is created, to release the air through a valve and onto a striker. This then forces the striker to travel down a guide tube and impact an anvil, which holds the broach and/or other surgical implement. However, this arrangement, due to the pressure of the air, can result in the generation of large forces on the tool's gear train and linear motion converter components that lead to premature wear on components.

Accordingly, there remains a need for improved surgical impacting tools.

SUMMARY

In general, gas spring surgical impacting tools and methods of using gas spring surgical impacting tools are provided.

In one aspect, a surgical tool is provided that in one embodiment includes a housing, a surgical implement configured to extend from a forward end of the housing and configured to engage bone, and a gas spring assembly disposed in the housing. The gas spring assembly includes a sealed chamber configured to contained compressed gas therein. The gas spring assembly is configured to alternately provide a forward force to the surgical implement configured to cause the surgical implement to move in a forward direction relative to the housing, and a rearward force to the surgical implement configured to cause the surgical implement to move in a rearward direction relative to the housing.

The surgical tool can have any number of variations. For example, the chamber and the surgical implement can be aligned along a longitudinal axis defined by the chamber, an opening can be formed in a wall of the chamber, the gas can be configured to be introduced into the chamber through the opening and then the opening sealed, and a longitudinal axis extending through the opening can be substantially perpendicular to the longitudinal axis defined by the chamber. In some embodiments, the gas spring assembly can include a screw seated in and sealing the opening, and a longitudinal axis of the screw can be substantially perpendicular to the longitudinal axis defined by the chamber.

For another example, the gas spring assembly can include an anvil and can include a piston, the piston can be configured to strike a first surface of the anvil in response to compression of the gas in the chamber such that the forward force is provided to the surgical implement, and the piston can be configured to strike a second, different surface of the anvil in response to compression of the gas in the chamber such that the rearward force is provided to the surgical implement. In some embodiments, the surgical tool can also include a motor configured to drive movement of the piston that causes the piston to alternately strike the first and second surfaces, the gas spring assembly can include a bumper located in the chamber, operatively coupled to the piston, and configured to bump against an inner surface of the chamber, and/or the piston can include a first piston configured to strike the first surface and a second piston configured to strike the second surface.

For yet another example, the housing can include a handle configured to be handheld by a user. For still another example, the gas spring assembly can define a constant force spring. For another example, the surgical implement can include a chisel or a broach.

In another embodiment, a surgical tool includes a first piston, a second piston, a first strike surface, a second strike surface, a sealed chamber, and a motor. The chamber is configured to contain compressed gas therein and defines a longitudinal axis extending between forward and rearward ends of the chamber. The first and second pistons are each positioned along the longitudinal axis of the chamber. The motor is configured to drive movement of the first piston in a first direction and to drive movement of the first piston in a second direction that is opposite to the first direction. The movement of the first piston in the first direction is configured to cause compression of the gas in the chamber and the first piston to strike the first strike surface and thereby communicate a rearward force to an end effector operatively coupled to the first piston, and the movement of the first piston in the second direction is configured to cause compression of the gas in the chamber and the second piston to strike the second strike surface and thereby communicate a forward force to the end effector operatively coupled to the second piston.

The surgical tool can vary in any number of ways. For example, an opening can be formed in a wall of the chamber, the gas can be configured to be introduced into the chamber through the opening and then the opening sealed, and a longitudinal axis extending through the opening can be substantially perpendicular to the longitudinal axis extending between the first and second ends of the chamber. In some embodiments, the surgical tool can also include a screw seated in and sealing the opening, and a longitudinal axis of the screw can be substantially perpendicular to the longitudinal axis extending between the first and second ends of the chamber.

For another example, the surgical tool can also include an anvil, and the anvil can include the first and second strike surfaces.

For yet another example, the surgical tool can also include a first shaft with a helical thread thereon, the movement of the first piston in the first and second directions can be translational movement, and the motor can be configured to cause rotation of the first shaft and thereby drive the translational movement of the first piston. In some embodiments, the surgical tool can also include an anvil and a second shaft extending radially outward, the second shaft can be configured to slide along the helical thread in response to the rotation of the first shaft, and the anvil can include the first and second strike surfaces.

For still another example, the surgical tool can also include a first bumper located in the chamber, operatively coupled to the first piston, and configured to bump against a rearward inner surface of the chamber; and a second bumper located in the chamber, operatively coupled to the second piston, and configured to bump against a forward inner surface of the chamber.

For still another example, the surgical tool can also include a housing in which the first piston, the second piston, the first strike surface, the second strike surface, and the sealed chamber are disposed. In some embodiments, the housing is configured to be handheld by a user.

For yet another example, the end effector can include a chisel or a broach.

In another aspect, a surgical method is provided that in one embodiment includes positioning, relative to bone, a surgical implement extending from a forward end of a housing of a surgical tool, and driving a gas spring assembly of a surgical tool using a motor and thereby compressing gas in a sealed chamber of the surgical tool so as to alternately provide a forward force to the surgical implement that causes the surgical implement to move in a forward direction relative to the housing and to the bone, and a rearward force to the surgical implement configured that causes the surgical implement to move in a rearward direction relative to the housing and the bone.

The surgical method can vary in any number of ways. For example, the chamber and the surgical implement can be aligned along a longitudinal axis defined by the chamber, an opening can be formed in a wall of the chamber, the gas can be configured to be introduced into the chamber through the opening and then the opening sealed, and a longitudinal axis extending through the opening can be substantially perpendicular to the longitudinal axis defined by the chamber.

For another example, the gas spring assembly can include an anvil and can include a piston, the piston can strike a first surface of the anvil in response to compression of the gas in the chamber such that the forward force is provided to the surgical implement, and the piston can strike a second, different surface of the anvil in response to compression of the gas in the chamber such that the rearward force is provided to the surgical implement. In some embodiments, the piston can include a first piston that strikes the first surface and a second piston that strikes the second surface.

For yet another example, the surgical implement can include a chisel or a broach. For still another example, the gas spring assembly can define a constant force spring.

BRIEF DESCRIPTION OF DRAWINGS

The present invention is described by way of reference to the accompanying figures which are as follows:

FIG. 3 is a front view of the tool of FIG. 1;

FIG. 4 is a side transparent exploded view of another embodiment of a surgical impacting tool;

FIG. 5 is a back view of the tool of FIG. 4;

FIG. 6 is a front view of the tool of FIG. 4;

DETAILED DESCRIPTION

Figure 1:
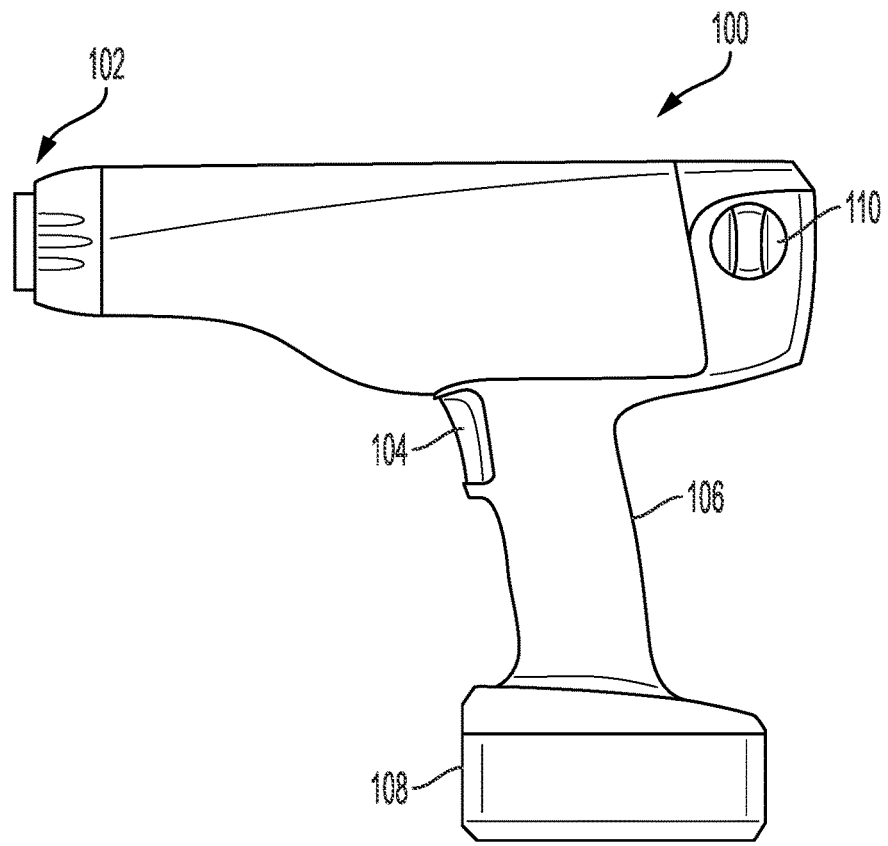
FIG. 1 is a side view of an embodiment of a surgical impacting tool.

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Various exemplary gas spring surgical impacting tools and methods of using gas spring surgical impacting tools are provided. In general, a surgical impacting tool includes a gas spring assembly. The gas spring assembly includes a sealed chamber configured to contained compressed gas therein. The surgical impacting tool also includes a motor configured to cause compression of the gas in the sealed chamber. The compression and decompression of the gas is configured to drive movement of a surgical implement attached to the surgical impacting tool and configured to impact bone. Impacting being driven using the gas spring assembly may help prevent stalling of the motor by allowing a current of the motor to be substantially constant while the motor is driving the impacting since a torque of the motor can be substantially constant to compress the gas. The gas chamber assembly may thus act like a constant force spring. Other impacting techniques that use a motor, such as techniques using a linear compressor, cannot consistently, if at all, achieve substantially constant motor current during impacting, thereby risking motor stall.

Impacting being driven using the gas spring assembly may help reduce noise during impacting because the motor is not driving a mechanical spring to compress or decompress, so mechanical spring decompression cannot cause a ringing or clang sound that can distract a user, obscure other important noises (e.g., talking between medical professionals performing a surgery, patient monitor beeping, etc.), and/or cause a user to think that the surgical impacting tool is not working properly. Additionally, the mechanical spring retains energy that causes the ringing or clang sound, so not all energy is delivered for impacting. Conversely, the gas spring assembly may be more efficient by delivering all energy for impacting.

The gas spring assembly may be inches smaller than a mechanical spring would need to be to similarly drive impacting, which may free tool space that would be occupied by the mechanical spring for other tool component(s) and/or may help make the surgical impacting tool smaller and thus lighter and/or easier for a user to hold while providing a similar impacting force. Mechanical springs can fatigue over time, e.g., metal fatigue due to repeated compression and decompression, and fail, unlike a gas spring assembly.

The surgical impacting tool is configured to provide a force to the surgical implement, using the motor and the gas spring assembly, to drive the impacting of the surgical implement. Whether the force is a forward driving force for forward impacting or a rearward driving force for rearward impacting, the force is a longitudinal force along the longitudinal axis defined by the sealed chamber.

The gas can be introduced into the chamber through an opening formed in a wall of the chamber, and then the opening can be closed to seal the chamber with the gas compressed therein. The chamber being sealed prevents the gas from being affected by atmospheric pressure. Atmospheric pressure is different at different elevations, so the chamber being sealed may allow for consistent impacting regardless of an elevation at which the surgical impacting tool is used. The gas can be compressed in the chamber at a pressure higher than standard atmospheric pressure, which is about 14.7 psi, because the chamber is sealed. For example, the gas in the chamber can have a pressure that is greater than standard atmospheric pressure, e.g., a pressure in a range of about 200 psi to about 400 psi, a pressure in a range above atmospheric pressure and up to and including about 20 psi, etc. Different energies can be provided by different pressures of gas in the sealed chamber, which may allow for energy control by compressing the gas in the chamber at a selected pressure to allow for a particular energy.

The chamber can be sealed with a screw or other mechanical element so as to be a static valve. The surgical impacting tool thus does not need to include a fill valve to fill the chamber with gas, which may help the surgical impacting tool be repeatedly sterilized, such as with autoclaving, for tool reuse because fill valves include multiple components that can be susceptible to failure during sterilization. In an exemplary embodiment, a longitudinal axis extending through the opening is substantially perpendicular to the longitudinal axis defined by the sealed chamber. The screw or other mechanical element seated in and closing the opening may thus not be jostled into unscrewing or into moving longitudinally during impacting because the force along the longitudinal axis defined by the sealed chamber is substantially perpendicular to the longitudinal axis extending through the opening and thus to a longitudinal axis of the screw or other mechanical element seated in and closing the opening. The chamber may thus remain tightly sealed over time as the surgical impacting tool is used.

The surgical implement can be a broach, chisel, or other surgical implement. The surgical impacting tool can be configured to releasably attach to the surgical implement. Each of the surgical implements configured to be attached to an surgical impacting tool can be different from one another in shape and/or size, thereby allowing for a particular surgical implement to be selected by a surgeon (or other medical professional) for optimal desired impacting in a particular surgical procedure being performed on a particular patient's bone. The surgical impacting tool can include an adapter configured to facilitate releasable attachment of the surgical implement to the surgical impacting tool. In some embodiments, instead of the surgical implement being releasably attachable to the surgical impacting tool, the surgical implement can be non-releasably attached to the surgical impacting tool.

Figure 2:
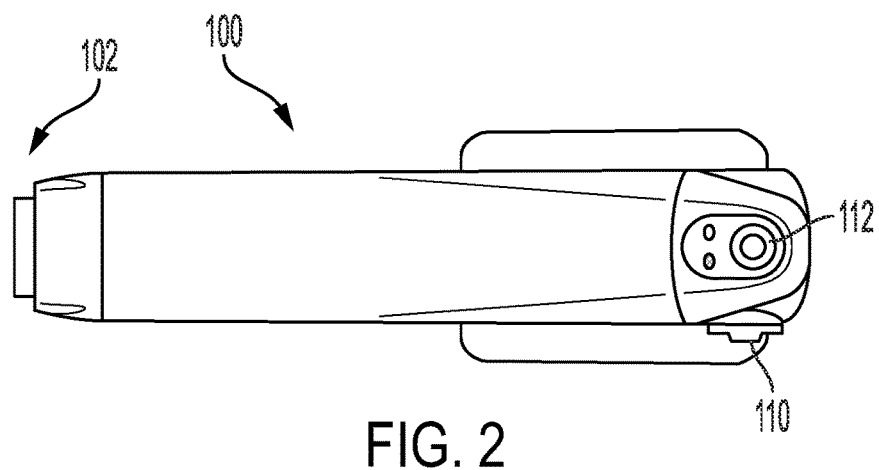
FIG. 2 is a top view of the tool of FIG. 1.
Figure 7:
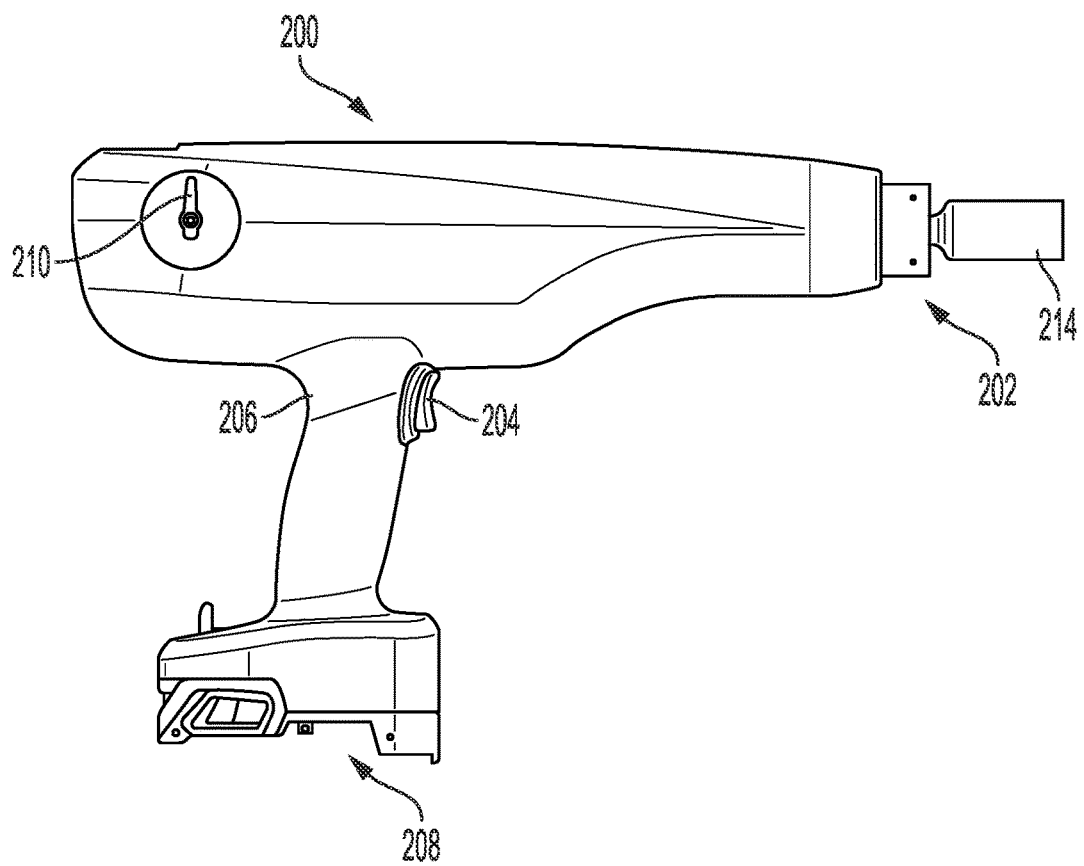
FIG. 7 is a side view of the tool of FIG. 4.
Figure 8:
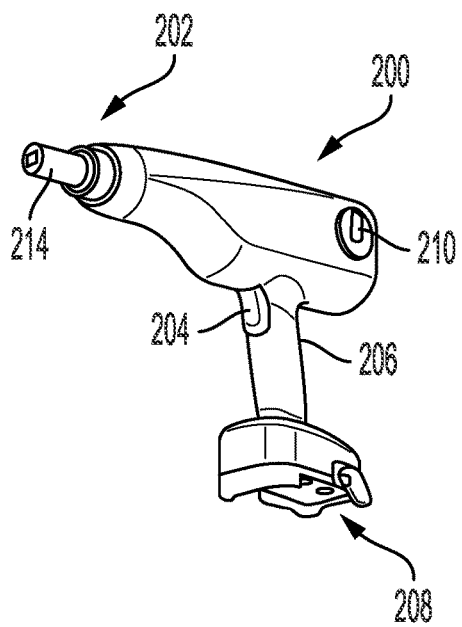
FIG. 8 is a perspective view of the tool of FIG. 4.
Figure 9:
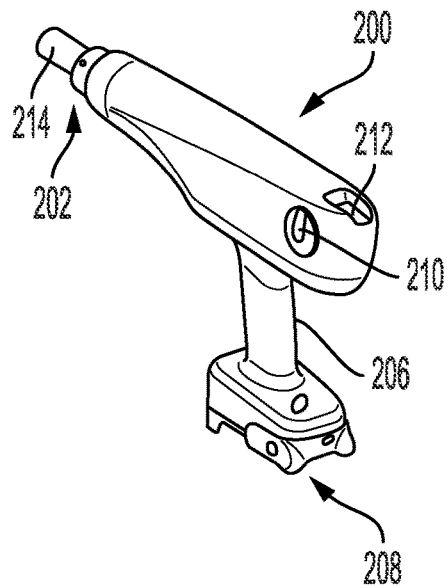
FIG. 9 is another perspective view of the tool of FIG. 4.

FIGS. 1-3 illustrate one embodiment of a surgical impacting tool 100 including a gas spring assembly (obscured by a housing 106 in FIGS. 1-3). The surgical impacting tool 100 is an orthopedic impactor in this illustrated embodiment, but as mentioned above, the surgical impacting tool 100 can be another type of surgical impacting tool. Embodiments of the gas spring assembly are discussed further below.

The surgical impacting tool 100 includes an actuator 104 configured to be actuated to cause a motor (obscured by the housing 106 in FIGS. 1-3) of the surgical impacting tool 100 to drive a surgical implement that is releasably attached to the surgical impacting tool 100, e.g., releasably attached thereto via an adapter at a forward end 102 of the surgical impacting tool. The actuator 104 in this illustrated embodiment includes a trigger on the housing 106 of the surgical impacting tool 100, but other surgical impacting tools can be actuated in other ways. In an exemplary embodiment, the surgical impacting tool 100 is configured to provide forward impacting, in which a forward force is provided by the surgical impacting tool for impacting in a forward direction, and rearward impacting, in which a rearward force is provided by the surgical impacting tool for impacting in a rearward direction. The forward and rearward impacting can be cyclical with sequential repeated forward and rearward impacts.

A power source 108 is configured to releasably attached to the housing 106 of the surgical impacting tool 100. The power source 108 includes a battery in this illustrated embodiment, but other power sources are possible. In other embodiments, the surgical impacting tool 100 can be releasably attachable to a power source in another way, such as by being plugged into a power source. In still other embodiments, the power source can be non-releasably attached to the surgical impacting tool 100, such as by a battery being non-removably disposed in the housing 106.

The surgical impacting tool 100 includes an energy selector 110 on the housing 106 of the surgical impacting tool 100. The energy selector 110 includes a rotary dial in this illustrated embodiment but can have other configurations, such as a lever, a button, etc. The energy selector 110 is configured to allow an energy level to be selected, e.g., high energy or low energy.

The surgical impacting tool 100 includes a frequency control 112 on the housing 106 of the surgical impacting tool 100. The frequency control 112 includes a button in this illustrated embodiment but can have other configurations, such as a lever, a rotary dial, etc. The frequency control 112 is configured to allow a frequency of impacts to be selected by a user, e.g., slow impacts or fast impacts.

The surgical impacting tool 100 can have additional or alternate features. Various exemplary embodiments of adapters and various exemplary embodiments of surgical impacting tools including additional or alternate features are further described in U.S. Pat. Pub. No. 2013/0161050 entitled "Electric Motor Driven Tool For Orthopedic Impacting" published Jun. 27, 2013, U.S. Pat. Pub. No. 2019/0183555 entitled "Orthopedic Adapter For An Electric Impacting Tool" published Jun. 20, 2019, U.S. Pat. Pub. No. 2018/0055552 entitled "Orthopedic Impacting Device Having A Controlled, Repeatable Impact" published Mar. 1, 2018, U.S. Pat. Pub. No. 2018/0055554 entitled "Orthopedic Impacting Device Having A Launched Mass Delivering A Controlled, Repeatable & Reversible Impacting Force" published Mar. 1, 2018, U.S. Pat. Pub. No. 2018/0338751 entitled "Orthopedic Device Delivering A Controlled, Repeatable Impact" published Nov. 29, 2018, U.S. Pat. No. 8,393,409 entitled "Electric Motor Driven Tool For Orthopedic Impacting" issued Mar. 12, 2013, U.S. Pat. No. 8,936,105 entitled "Electric Motor Driven Tool For Orthopedic Impacting" issued Jan. 20, 2015, and U.S. Pat. No. 8,695,726 entitled "Electric Motor Driven Tool For Orthopedic Impacting" issued Apr. 15, 2014, which are hereby each incorporated by reference in their entirety.

FIGS. 4-9 illustrate another embodiment of a surgical impacting tool 200 including a gas spring assembly 202. The surgical impacting tool 200 is an orthopedic impactor in this illustrated embodiment, but as mentioned above, the surgical impacting tool 200 can be another type of surgical impacting tool. The surgical impacting tool 200 is generally configured and used similar to the surgical impacting tool 100 of FIG. 1, e.g., includes an adapter 214 at a forward end 200f of the surgical impacting tool 200 and includes the gas spring assembly 202, an actuator 204 (not shown in FIG. 4), a housing 206, an energy selector 210 (which is a lever in this illustrated embodiment), a frequency control 212 (which is a dial in this illustrated embodiment), and a motor 216. The surgical impacting tool 200 in this illustrated embodiment is configured at a bottom end 208 of the surgical impacting tool 200 to releasably attach to a power source 218, similar to the surgical impacting tool 100 being releasably attachable to the power source 108 as discussed above.

The adapter 214 in this illustrated embodiment is configured to releasably attach to a surgical implement to impact bone. In other embodiments, the adapter 214 can be non-releasably attached to a surgical implement. Additionally, the adapter 214 in this illustrated embodiment is configured to releasably attach to the surgical impacting tool 200 but in other embodiments can be non-releasably attached to the surgical impacting tool 200. In other embodiments, a surgical implement can be attached to a surgical impacting tool without an adapter.

Figure 10:
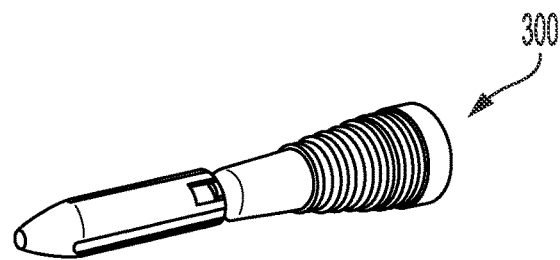
FIG. 10 is a perspective view of one embodiment of a surgical implement.
Figure 11:
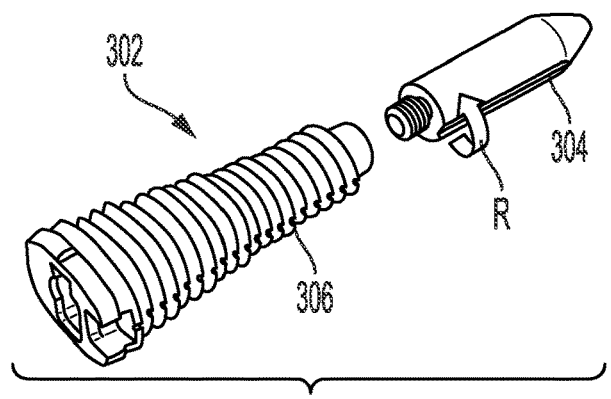
FIG. 11 is a perspective view of another embodiment of a surgical implement.
Figure 12:
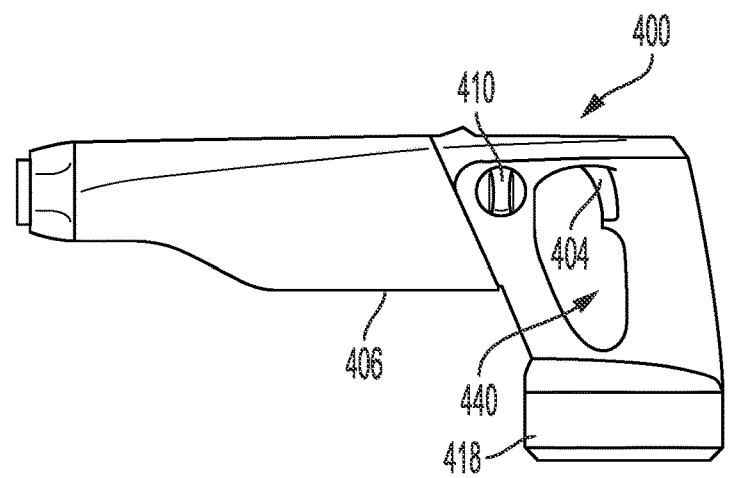
FIG. 12 is a side view of another embodiment of a surgical impacting tool.
Figure 13:
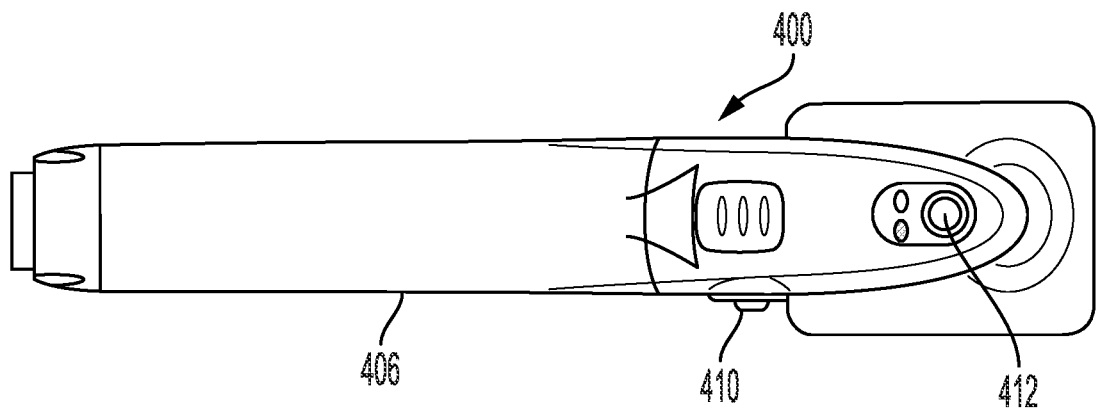
FIG. 13 is a top view of the tool of FIG. 12.
Figure 14:
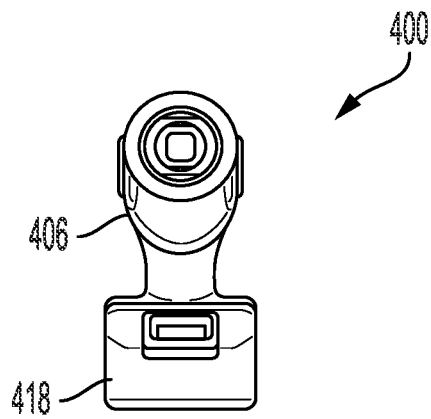
FIG. 14 is a front view of the tool of FIG. 12.
Figure 15:
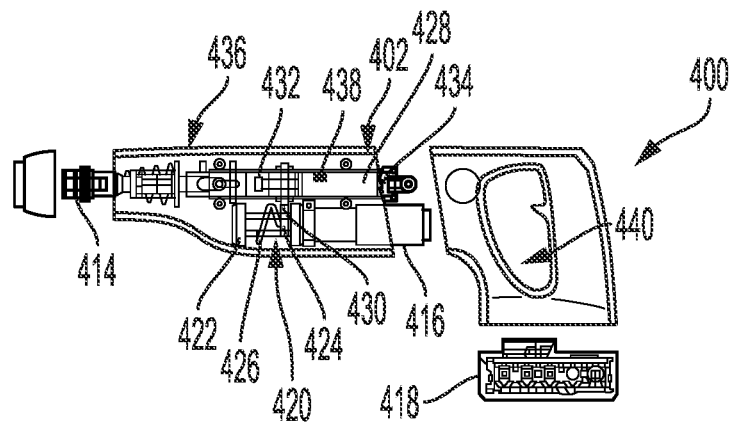
FIG. 15 is a side transparent exploded view of the tool of FIG. 12.

As mentioned above, various surgical implements such as chisels and broaches can be configured to releasably attach to the adapter 214. FIG. 10 illustrates one embodiment of a surgical implement 300 configured to releasably attach to the adapter 214. The surgical implement 300 in this illustrated embodiment is a tibial broach configured for impacting a tibia. FIG. 11 illustrates another embodiment of a surgical implement 302 configured to releasably attach to the adapter 214. The surgical implement 302 in this illustrated embodiment is a femoral broach configured for impacting a femur. The surgical implement 302 in this illustrated embodiment includes a forward portion 304 and a rearward portion 306 that is configured to releasably attach to the forward portion 304 by rotating the forward portion 304 into the rearward portion 306 as shown by arrow R.

The motor 216 can have a variety of configurations. In an exemplary embodiment, the motor 216 is electric, such as a brushless, autoclavable motor such as those generally available from Maxon Motor® and those available from Portescap®.

The surgical impacting tool 200 also includes a cam 220 that is operatively coupled to the motor 216 by being mounted on a shaft (obscured in FIG. 4) extending from the motor 216 to a bearing support 222. The motor 216 is configured to drive rotation of the cam 220 by causing rotation of the shaft. The cam 220 includes a barrel 224 and a worm 226 protruding radially outward from and extending helically along the barrel 224. The barrel 224 is substantially cylindrical. A person skilled in the art will appreciate that a shape may not be precisely cylindrical but nevertheless be considered to be substantially cylindrical due to any number of factors, such as manufacturing tolerances and sensitivity of measurement equipment. The rotation of the cam 220 includes rotation of the barrel 224 and the worm 226 protruding therefrom.

The gas spring assembly 202 includes a sealed chamber 228, a cam follower 230 that extends radially outward, a forward piston 232 that extends forwardly, and a rearward piston 234 that extends rearwardly. The cam follower 230 and is operatively engaged with the cam 220, in particular with the worm 226 of the cam 220.

The motor 216 is configured to drive rotation of the cam 220 in a first direction to cause forward impacting via the forward piston 232 and to drive rotation of the cam 220 in a second, opposite direction to cause rearward impacting via the rearward piston 234. In this illustrated embodiment, the first direction is counterclockwise, and the second direction is clockwise. The first and second directions can be reversed, e.g., by reversing helical wrapping of the worm 226.

The motor 216 being actuated, e.g., via the trigger 204, to rotate the shaft and the cam 220 in the first direction causes the cam follower 230 to slide along a surface of the worm 226, which causes gas in the sealed chamber 228 to compress and thereby store potential energy. The cam's rotation in the first direction will eventually cause a rearward terminal end of the worm 226 to move past the cam follower 230, which frees the cam follower 230 from the guide of the cam 220, e.g., of the worm 226. The gas in the sealed chamber 228 is thus free to decompress in a forward direction as the cam follower 230 moves from the rearward terminal end of the worm 226 to a forward terminal end of the worm 226. The decompression of the gas, e.g., the release of the potential energy, as the cam follower 230 moves forwardly causes the rearward piston 234 to strike a first strike surface of the surgical impacting tool 200. The first strike surface in this illustrated embodiment is a first surface of an anvil 236 of the surgical impacting tool 200. The impact of the rearward piston 234 communicates a forwardly directed force to the surgical implement via the adapter 214.

The motor 216 being actuated, e.g., via the trigger 204, to rotate the shaft and the cam 220 in the second direction causes the cam follower 230 to slide along a surface of the worm 226, which causes gas in the sealed chamber 228 to compress and thereby store potential energy. The cam's rotation in the second direction will eventually cause the forward terminal end of the worm 226 to move past the cam follower 230, which frees the cam follower 230 from the guide of the cam 220, e.g., of the worm 226. The gas in the sealed chamber 228 is thus free to decompress in a rearward direction as the cam follower 230 moves from the forward terminal end of the worm 226 to the rearward terminal end of the worm 226. The decompression of the gas, e.g., the release of the potential energy, as the cam follower 230 moves rearwardly causes the forward piston 232 to move rearwardly and strike a second strike surface of the surgical impacting tool 200. The second strike surface in this illustrated embodiment is a second, different surface of the anvil 236. The impact of the forward piston 232 communicates a rearwardly directed force to the surgical implement via the adapter 214.

Whether the force communicated to the surgical implement is directed forwardly or rearwardly, the force is communicated longitudinally along a longitudinal axis A1 defined by the sealed chamber 228 with which the surgical implement is aligned. The rotary motion of the cam 220 driven by the motor 216 is thus converted to translational motion to allow for longitudinal impacting.

The chamber 228 is configured to be filled with the gas through an opening formed in a wall of the chamber 228. Then, with the gas in the chamber 228, the opening is configured to be closed by seating a mechanical element 238, e.g., a screw, a plug, or other element, in the opening. FIG. 4 shows the mechanical element 238 seated in the opening and with the chamber 228 sealed.

The opening defines a longitudinal axis A2. The mechanical element 238 thus extends along the longitudinal axis A2 defined by the opening. The longitudinal axis A2 defined by the opening is substantially perpendicular to the longitudinal axis A1 defined by the chamber 228 and is thus substantially perpendicular to the direction of the impact force. Being substantially perpendicular to the opening and the mechanical element 238 seated therein, the impact force will thus not urge movement of the mechanical element 238 to cause jostling of the mechanical element 238 in the opening along the opening's longitudinal axis A2 or any unscrewing of the mechanical element 238 (in embodiments in which the mechanical element 238 is a screw). The chamber 228 may thus remain tightly sealed over time as the surgical impacting tool 200 is used. A person skilled in the art will appreciate that axes may not be precisely perpendicular but nevertheless be considered to be substantially perpendicular due to any number of factors, such as manufacturing tolerances and sensitivity of measurement equipment.

FIGS. 12-15 illustrate another embodiment of a surgical impacting tool 400 including a gas spring assembly 402. The surgical impacting tool 400 is an orthopedic impactor in this illustrated embodiment, but as mentioned above, the surgical impacting tool 400 can be another type of surgical impacting tool. The surgical impacting tool 400 is generally configured and used similar to the surgical impacting tool 100 of FIG. 1 and the surgical impacting tool 200 of FIG. 4, e.g., includes an adapter 414, an actuator 404 (not shown in FIG. 15), a housing 406, an energy selector 410 (which is a rotary dial in this illustrated embodiment), a frequency control 412 (which is a button in this illustrated embodiment), a motor 416, a power source 418, a cam 420, a bearing support 422, an anvil 436, and a shaft (obscured in FIG. 15) extending between the motor 416 and the bearing support 422. The surgical impacting tool 400 in this illustrated embodiment is configured at a bottom end of the surgical impacting tool 400 to releasably attach to a power source, similar to the surgical impacting tool 100 being releasably attachable to the power source 418 as discussed above. The cam 420 is generally configured and used similar to the cam 220 of FIG. 4, e.g., includes a barrel 424 and a worm 426 protruding radially outward from and extending helically along the barrel 424. The gas spring assembly 402 is generally configured and used similar to the gas spring assembly 202 of FIG. 4, e.g., includes a sealed chamber 428, a cam follower 430 that extends radially outward, a forward piston 432 that extends forwardly, a rearward piston 434 that extends rearwardly, and a mechanical element 438 seated in an opening in a wall of the chamber 428. In this illustrated embodiment, the housing 406 has a different shape than the housings 106, 206 and defines an opening 440 configured to receive fingers therethrough to facilitate hand-holding of the surgical impacting tool 400.

Figure 16:
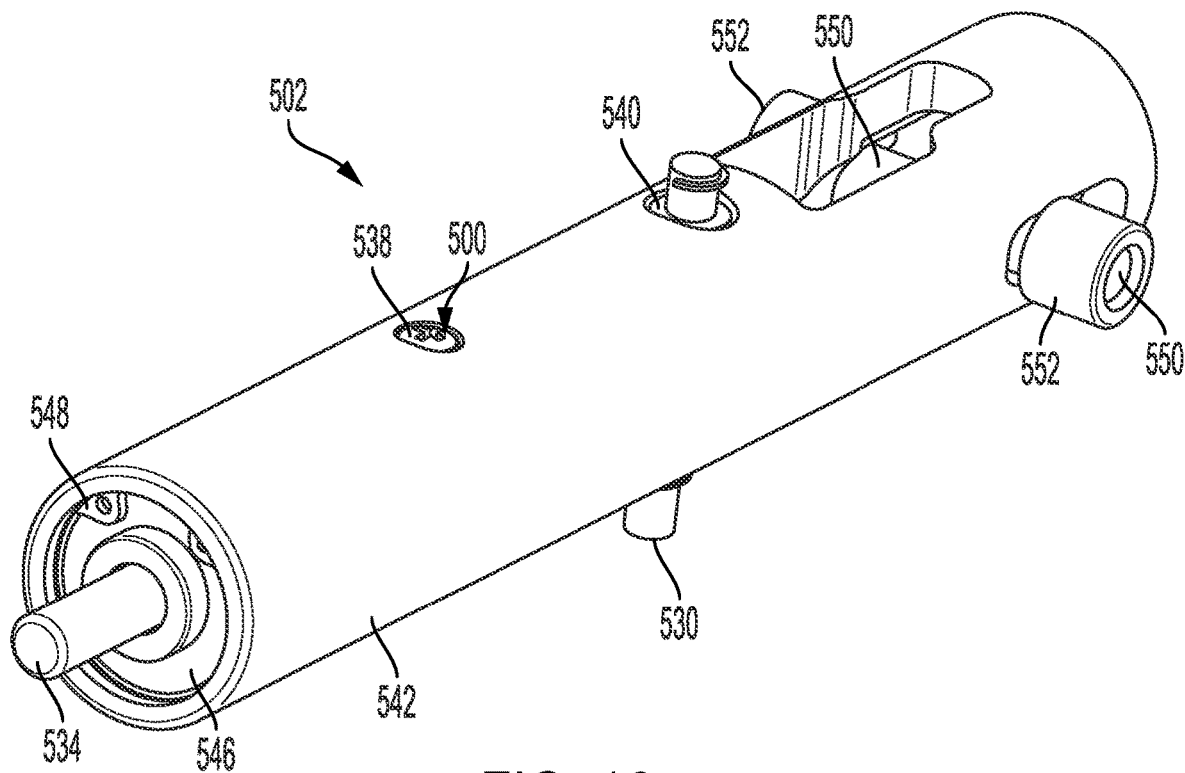
FIG. 16 is a perspective view of one embodiment of a gas spring assembly.
Figure 17:
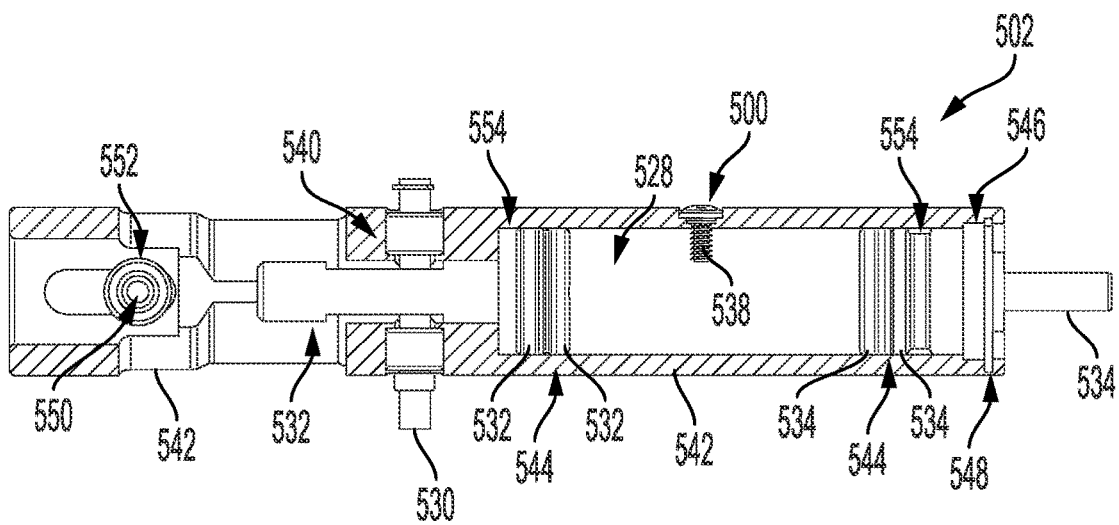
FIG. 17 is a side cross-sectional view of the gas spring assembly of FIG. 16.

FIGS. 16 and 17 illustrate another embodiment of a gas spring assembly 502 that can be used as a gas spring assembly of a surgical impacting tool, such as in place of the gas spring assembly of the surgical impacting tool 100 of FIGS. 1-3, the gas spring assembly 202 of the surgical impacting tool 200 of FIGS. 4-9, the gas spring assembly 402 of the surgical impacting tool 400 of FIGS. 12-15, or the gas spring assembly of another embodiment of a surgical impacting tool. The gas spring assembly 502 is generally configured and used similar to the gas spring assembly 202 of FIG. 4, e.g., includes a sealed chamber 528, a cam follower 530 that extends radially outward, a forward piston 532 that extends forwardly, a rearward piston 534 that extends rearwardly, and a mechanical element 538 seated in an opening 500 in a wall of the chamber 528. The mechanical element 538 is a screw in this illustrated embodiment.

FIGS. 16 and 17 illustrate various features of the gas spring assembly 502 that can be similarly incorporated into the illustrated gas spring assemblies 202, 402 discussed above. The gas spring assembly 502 includes a pair of needle bearings 540 configured to facilitate attachment of the cam follower 530 to a main body 542 of the gas spring assembly 502. The needle bearings 540 are located on opposite sides of the chamber 528 in a radial direction to facilitate radial extension of the cam follower 530. The chamber 528 is a cavity formed in the body 542, and the opening 500 is formed in a wall of the body 542.

The gas spring assembly 502 includes a pair of seals 544 located at opposed forward and rearward ends of the chamber 528. The seals 544 are configured to seal the forward and rearward ends, respectively, of the chamber 528. The seals 544 are X-ring seals in this illustrated embodiments but can be another type of seal.

The gas spring assembly 502 includes a bushing 546 configured to attach the rearward piston 534 to the body 542 of the gas spring assembly 502. The piston 534 is movably seated in the bushing 546. The gas spring assembly 502 also includes a retaining ring 548 configured to retain the bushing 546 in the body 542.

The gas spring assembly 502 includes an anvil coupling rod 550 and a pair of anvil guide rollers 552. The rod 550 extends outside of and on opposite sides of the body 542, and the rollers 552 are disposed on the rod 550 outside of and on opposite sides of the body 542. The anvil coupling rod 550 and the pair of anvil guide rollers 552 are configured to attach to an anvil of the surgical impacting tool that includes the gas spring assembly 502. The anvil coupling rod 550 and the pair of anvil guide rollers 552 may thus securely fix the gas spring assembly 502 to the anvil to help ensure effective impacts of the pistons 532, 534 on surfaces of the anvil.

The gas spring assembly 502 includes a pair of bumpers 554 located at opposed forward and rearward ends of the chamber 528. The forward bumper 554 is operatively coupled to the forward piston 532, and the rearward bumper 554 is operatively coupled to the rearward piston 534. Bottoms of each of the forward and rearward pistons 532, 534 are located inside of the chamber 528, as shown in FIG. 17. The bumpers 554 are configured to prevent the forward and rearward pistons 532, 534, e.g., the bottoms thereof, from striking a wall of the chamber 528, which could damage the body 524 and/or the pistons 532, 534. The forward bumper 554 is positioned between a forward wall of the chamber 528 and the bottom of the forward piston 532 and is configured to bump against a surface of the forward wall of the chamber 528. The rearward bumper 554 is positioned between a rearward wall of the chamber 528 and the bottom of the rearward piston 534 and is configured to bump against a surface of the rearward wall of the chamber 528. The seals 554 are positioned inward of the bumpers 554, so the bumpers 554 being located in the chamber 528 do not affect the sealed nature of the chamber 528 in which the gas is located for compression/decompression. The bumpers 554 can be made from a resilient material, such as a plastic, a rubber, or urethane material.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical tool, comprising:
a first piston;
a second piston that is independent from the first piston and is located rearward of the first piston;
a first strike surface;
a second strike surface;
a sealed chamber configured to contain compressed gas therein, the chamber defining a longitudinal axis extending between forward and rearward ends of the chamber, the first and second pistons each being positioned along the longitudinal axis of the chamber; and
a motor configured to drive movement of the first piston in a first direction and to drive movement of the first piston in a second direction that is opposite to the first direction, the movement of the first piston in the first direction being configured to cause compression of the gas in the chamber and the first piston to strike the first strike surface and thereby communicate a rearward force to an end effector operatively coupled to the first piston, and the movement of the first piston in the second direction being configured to cause compression of the gas in the chamber and the second piston to strike the second strike surface and thereby communicate a forward force to the end effector operatively coupled to the second piston.

2. The tool of claim 1, wherein an opening is formed in a wall of the chamber;
the gas is configured to be introduced into the chamber through the opening and then the opening sealed;
the motor is configured to drive the movement of the first piston with chamber containing the compressed gas; and
a longitudinal axis extending through the opening is substantially perpendicular to the longitudinal axis extending between the first and second ends of the chamber.

3. The tool of claim 2, further comprising a screw seated in and sealing the opening;
wherein, with the screw sealing the opening, a longitudinal axis of the screw is substantially perpendicular to the longitudinal axis extending between the first and second ends of the chamber.

4. The tool of claim 1, further comprising an anvil, the anvil including the first and second strike surfaces.

5. The tool of claim 1, further comprising a first shaft with a helical thread thereon;
wherein the movement of the first piston in the first and second directions is translational movement; and
wherein the motor is configured to cause rotation of the first shaft and thereby drive the translational movement of the first piston.

6. The tool of claim 5, further comprising an anvil; and
a second shaft extending radially outward and being configured to slide along the helical thread in response to the rotation of the first shaft;
wherein the anvil includes the first and second strike surfaces.

7. The tool of claim 1, further comprising a first bumper located in the chamber, operatively coupled to the first piston, and configured to bump against a rearward inner surface of the chamber; and
a second bumper located in the chamber, operatively coupled to the second piston, and configured to bump against a forward inner surface of the chamber.

8. The tool of claim 1, further comprising a housing in which the first piston, the second piston, the first strike surface, the second strike surface, and the sealed chamber are disposed.

9. The tool of claim 8, wherein the housing is configured to be handheld by a user.

* * * * *